(12) United States Patent
Wolter

(10) Patent No.: US 8,076,441 B2
(45) Date of Patent: Dec. 13, 2011

(54) PROCESS FOR BRIDGING ORGANICALLY POLYMERIZABLE SILANES OR SILANE RESIN SYSTEMS CONTAINING HYDROXY- OR CARBOXYLIC ACID GROUPS AS WELL AS PRODUCTS OBTAINED WITH SAID PROCESS

(75) Inventor: Herbert Wolter, Tauberbischofsheim (DE)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 548 days.

(21) Appl. No.: 11/910,862

(22) PCT Filed: Apr. 18, 2006

(86) PCT No.: PCT/EP2006/003527
§ 371 (c)(1),
(2), (4) Date: Jun. 8, 2008

(87) PCT Pub. No.: WO2006/111352
PCT Pub. Date: Oct. 26, 2006

(65) Prior Publication Data
US 2008/0319127 A1   Dec. 25, 2008

(30) Foreign Application Priority Data
Apr. 19, 2005 (DE) .......................... 10 2005 018 059

(51) Int. Cl.
*C08G 77/00* (2006.01)
(52) U.S. Cl. .......... 528/26; 556/413; 556/436; 556/437; 556/418; 556/419; 524/588; 528/28
(58) Field of Classification Search .................. 528/1–35
See application file for complete search history.

(56) References Cited

U.S. PATENT DOCUMENTS

| | | | |
|---|---|---|---|
| 4,243,692 A | 1/1981 | Scholze et al. | |
| 5,399,738 A | 3/1995 | Wolter et al. | |
| 5,414,093 A | 5/1995 | Wolter | |
| 5,717,125 A | 2/1998 | Wolter et al. | |
| 5,889,132 A | 3/1999 | Rheinberger et al. | |
| 5,919,885 A | 7/1999 | Wolter et al. | |
| 6,124,491 A | 9/2000 | Wolter et al. | |
| 6,222,055 B1 | 4/2001 | Wolter et al. | |
| 6,794,527 B1 * | 9/2004 | Wolter et al. | 556/419 |
| 2005/0165129 A1 * | 7/2005 | Moszner et al. | 523/115 |
| 2006/0171990 A1 * | 8/2006 | Asgari | 424/426 |

FOREIGN PATENT DOCUMENTS

| | | |
|---|---|---|
| DE | 27 58 414 A1 | 12/1977 |
| DE | 40 11 044 A1 | 4/1990 |
| DE | 41 25 201 C1 | 7/1991 |
| DE | 41 33 494 A1 | 10/1991 |
| DE | 44 05 261 A1 | 2/1994 |
| DE | 44 16 857 C1 | 5/1994 |
| DE | 44 16 857 C1 | 6/1995 |
| DE | 195 25 562 A1 | 7/1995 |
| DE | 196 19 046 A1 | 5/1996 |
| DE | 199 10 895 A1 | 3/1999 |
| EP | 0 450 624 B1 | 4/1991 |
| EP | 0 451 709 B1 | 4/1991 |
| EP | 0 230 342 B1 | 8/1992 |
| EP | 0 682 033 A | 11/1995 |
| EP | 0 837 897 B1 | 7/1996 |
| EP | 0 643 752 B1 | 9/1999 |
| EP | 1 022 012 A | 7/2000 |
| JP | 11-35895 | 2/1999 |
| WO | WO 98/28307 | 7/1998 |

\* cited by examiner

*Primary Examiner* — Marc Zimmer
*Assistant Examiner* — Lindsay Nelson
(74) *Attorney, Agent, or Firm* — Stephen A. Bent; Foley & Lardner LLP

(57) ABSTRACT

The present invention relates to a process for cross-linking a silane with the structure (IIa)

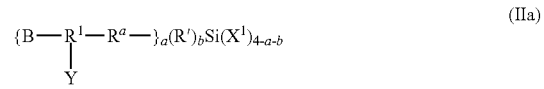

for the preparation of a product, comprising component (III)

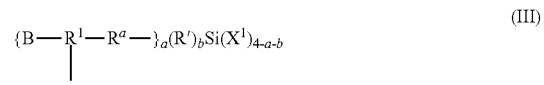

twice, in triplicate or in a higher quantity, where the radicals B, $R^1$, $R^a$, R', $X^1$ and the indices a and b are defined as above for structure (IIa) and can be identical or different in each case,
or for the cross-linking of a condensate, a partial condensate, a polymer or a partial polymer comprising structural units with the structure (IIb)

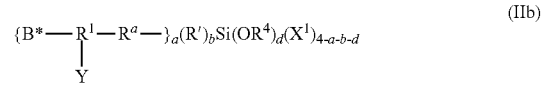

via the bond $R^1$—,
characterized in that a silane with the structure (IIa), or an isomer, a re-esterification product or a condensation product of said silane, which condensation product was formed by loss of an alcohol molecule, or a condensate, a partial condensate, a polymer, or a partial polymer comprising structural units of structure (IIb) is reacted with a compound having the structure (IV)

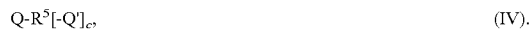

22 Claims, No Drawings

PROCESS FOR BRIDGING ORGANICALLY POLYMERIZABLE SILANES OR SILANE RESIN SYSTEMS CONTAINING HYDROXY- OR CARBOXYLIC ACID GROUPS AS WELL AS PRODUCTS OBTAINED WITH SAID PROCESS

The present invention relates to a process for the production of novel silanes with two, three, or even more structural units which are cross-linked with each other via a bridge containing urethane, acid amide and/or carboxylic acid ester (carboxylate) groups and wherein each of said units contains at least one organically polymerizable radical and at least one silyl radical. These silanes are particularly suitable for the modification of the properties of silicic acid (hetero)polycondensates and silyl group-containing organic polymers (ORMOCER®s). The process according to the invention is also suitable for bridging already preconsensated silicic acid (hetero)polycondensates. The inventive process is a further development of the process described and claimed in DE 103 49 766.8.

Silicic acid heteropolycondensates, obtainable by hydrolysis and condensation of silanes with hydrolyzable groups, have been known for a long time (see, for example DE PS 27 58 414). Such condensates can be processed to form many products, for example, to form coverings, coatings, membranes, or bulk materials. The underlying silanes can also comprise double bonds or other organically reactive groups through which they can be polymerized into an organic network (see, for example DE 40 11 044 C2 and DE 44 05 261 A1). A quite specific group of such materials can be obtained from silicic acid polycondensates which comprise a radical bonded to the silicon atom, said radical comprising, in addition to at least one organically reactive group, a free hydroxy or carboxylic acid group. Such silicic acid polycondensates are described in DE 44 16 857 C1. They are suitable, alone, in mixtures, or together with other hydrolyzable, condensable, or polymerizable components, for the production of scratch-resistant coatings, filling materials, adhesive materials, sealing materials, shaped bodies, or embedded materials. The group of compounds described in DE 44 16 857 C1 is furthermore distinguished by the fact that the distance between the silicon atom and reactive or double bond(s) can be set arbitrarily, on account of which the physical characteristics of the condensates or polymerizates thus obtained can be set over wide ranges.

The carboxylic acid group of the carboxylic acid-modified silanes of DE 44 16 857 C1 are charge carriers and thus make possible, for example, the production of dispersions, emulsions, or electropaints. Furthermore, these groups can be complexed with suitable metal compounds of titanium, zirconium, tin, and others. The combination of carboxyl groups with polymerizable C=C double bonds in connection with the inorganic silane portion represents an ideal compound for use as polyalkene acids in ionomer cements. However, in many cases one needs systems with a lower hydrophilicity of the matrix than that of the condensates which are obtained from the compounds from DE 44 16 857 C1. It was the objective of the invention disclosed in DE 103 49 766.8 to provide such systems as well as the silanes needed for them.

This objective was realized by the preparation of silanes of the structure (I)

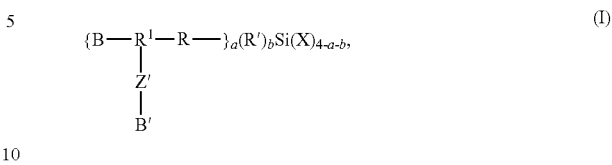

where the radicals and indices have the following meanings:
R is an open-chain and/or cyclic alkylene, arylene, or alkylene-arylene group, with 1 to 10 carbon atoms in each case, which can be interrupted in many cases by one or more oxygen or sulfur atoms or carboxyl or amino groups or can carry such atoms/groups at its end opposite the silicon atom; $R^1$ is an open-chain and/or cyclic alkylene, arylene, or alkylene-arylene group, with 1 to 10 carbon atoms in each case, which in many cases can be interrupted by one or more oxygen or sulfur atoms or carboxyl or amino groups or can carry such atoms/groups at its ends and which, as can be seen from structure (I), carries the group Z' as a substituent; R' is an open-chain and/or cyclic alkyl, alkenyl, aryl, or alkylaryl, or arylalkyl group, with preferably 1 to 10 carbon atoms; B and B' can be identical or different; both radicals can have the meaning of a straight-chain or branched organic group with at least one C=C double bond and at least 2, preferably up to 50, carbon atoms; however, instead of this, B' can also mean $-R^2{}_a SiX_{4-a}$ or $-R^2{}_a R'_b SiX_{4-a-b}$, where $R^2$ is an alkylene group with 1 to 10 carbon atoms and X is as defined below. X is a group which can enter into a hydrolytic condensation reaction with the formation of Si—O—Si bridges. Groups X are designated as inorganic network formers since a silicic acid polycondensate network can form in the hydrolytic condensation reaction. Z' has the meaning —NH—C(O)O—, —NH—C(O)—, or —CO(O)—, where the two radicals named first are bonded via the NH group to the radical B' while the carboxylate group can point in both directions, where, when Z' is a —CO(O)— group the carbon atom of which is bonded to the radical B', the grouping B'-Z'— must not have the meaning of an acrylate group if B comprises an acrylate group, and the grouping B'-Z'— must not represent a methacrylate group if B comprises a methacrylate group; a means 1 or 2, preferably 1, and b can be 0 or 1.

DE 103 49 766.8 thus provides silanes and silicic acid polycondensates or partial polycondensates derived therefrom which are synthesized with the use of structural elements which comprise a partially or completely hydrolyzable/hydrolyzed and/or condensable/condensed silane radical, at least one urethane, acid amide, or carboxylic acid ester group, and either at least two radicals which can be organically polymerized, are arranged so as to be branched, and comprise C=C double bonds, where one of these two radicals is bonded via the stated urethane, acid amide, or carboxylic acid ester group to the silicon atom, or one such organically polymerizable radical, and an additional radical comprising a silicon atom and bonded via the said urethane, acid amide, or carboxylic acid ester group to this organic radical.

As explained in detail further below, the silanes and the silicic acid polycondensates or partial polycondensates derived therefrom, according to DE 103 49 877.8, can be obtained starting from silanes which comprise a radical B as well as a hydroxy or is carboxyl group bonded to a linker between this radical B and the silicon atom. These are described in DE 44 16 857 C1.

Such silicic acid polycondensates can be organically cross-linked via the organically polymerizable portions of the radicals B and in given cases also B'. Thus, due to the presence of at least two organically cross-linkable groups per silane molecule, a system is obtained, the organic portion of which leads to a particularly high mechanical strength as well as to an improved shrinking behaviour with a reduced shrinkage. If B' instead is —R²$_a$SiX$_{4-a}$ order R²$_a$R'$_b$SiX$_{4-a-b}$, the silicon polycondensate in this embodiment can form a particularly dense Si—O—Si network due to the presence of a further silicon atom.

The compounds and condensates or (partial) condensates according to DE 103 49 766.8 can be obtained, for example, starting from compounds of the structure (IIa)

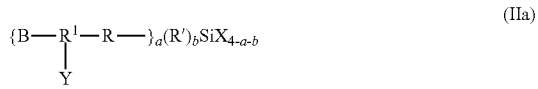

where B, R¹, R, R', X, a, and b have the meanings specified for the structure (I) and Y is OH or COOH. The radicals or substituents R' and X located at the silicon atom can be chosen in any manner. In the literature concerning the inorganic-organic materials containing silicon atoms, e.g., those which are commercially available under the name "ORMOCER"®s, much has been written about the respective properties which the respective silane radicals confer to the condensate or organically polymerizable network so that here no detailed explanations are needed.

Compounds of the structure (IIa) are known. Thus, for example, according to DE 44 16 857 C1 compounds of the structure (IIa) can be produced in which B has the meaning B"-Z—, where B" also has the meaning of a straight-chain or branched organic group with at least one C═C double bond and 2, preferably up to 50, carbon atoms with the preferred embodiments described for B, and Z is an —O—C(O)—, —S—C(O), or —NH—C(O)— group, and this can be done by addition reactions of cyclic carboxylic acid anhydride silanes of any ring size with compounds B" (AH), where AH is a hydroxy, a mercapto, or an amino group, where products are obtained in which Y means —COOH. If, instead of this, epoxide silanes are reacted with compounds B" (AH) in which AH is a hydroxy, a mercapto, an amino group, or a carboxylic acid radical, products are obtained in which Y means —OH and Z is —O—R", —S—R", —NH—R", —C(O)O—R", —O—, —S—, —NH—, or —C(O)O—. Therein R" has the above-specified meaning. The reaction commonly takes place without a catalyst if reacted with carboxylic acid anhydride silanes, and in most cases in the presence of a suitable catalyst, e.g., of tertiary amines such as triethylamine or phosphines such as triphenylphosphine, and optionally with increased temperatures if an epoxide silane is used.

In the above-described reactions for the production of the compounds of the structure (IIa), isomers and re-esterification products of these compounds can form, depending on the starting materials actually used. This is in particular the case to a significant extent when the radicals X are alkoxy groups, above all methoxy or ethoxy groups. Since in such isomers and re-esterification products the group Y is partially involved in the isomerization/re-esterification reaction, it is partially no longer free in these products. It has turned out that these byproducts can be drawn upon for the production of the condensates according to DE 103 49 877.8 just as well as the compounds of the structure (IIa) themselves, where a separation of the various products is not necessary at all. Instead of this it is sufficient to react the starting materials described for the production of the compounds with the structure (IIa) with one another in the specified manner and subsequently to subject them to a hydrolysis. In so doing, the group Y becomes surprisingly free once again while the re-formation of SiOH groups on the contrary turns out in varying amounts and can be essentially suppressed. Thus, as a rule a condensate with an Si—O—Si network is obtained.

The compounds of structure (IIa) or their condensation products with the group Y released once again are worked up if needed (for example, separated, washed, isolated) and/or, if necessary, dried. In so doing, it should be attended to in particular that no, or as little as possible, H-active impurities are present in the reaction mixture in order to avoid side reactions with the isocyanate in the reaction described below. Then they can be reacted with an isocyanate, where, when Y means OH, a product forms in which Z' is a urethane group —NH—C(O)O—, and if Y means COOH, Z' is an acid amide group —C(O)—NH—. Alternatively, they are reacted with a carboxylic acid or an activated carbonyl group (for example, an acid chloride or anhydride) (for Y equal to OH) or an alcohol (for Y equal to COOH) according to common processes, e.g., in the presence of activation agents such as dicyclohexylcarbodiimide, where an ester group —C(O)O— arises which, depending on the starting substances, can point in one or the other direction.

The compounds according to DE 103 49 766.8 are produced according to a reaction scheme which can be defined as follows:

A compound with structure (IIa), or an isomer, a re-esterification product thereof or a condensation product thereof which arose as a result of the loss of an alcohol molecule as described above, is reacted with a compound B'Q, where B' has the meaning specified for structure (I) and Q either means —NCO, or Q can mean —OH if Y is —COOH, or can mean —C(O)X if Y is OH where C(O)X' is a carboxylic acid group or an activated carbonyl compound, particularly an acid chloride or an acid anhydride.

If Y means OH in the compound with structure (IIa), a compound with structure (I) is formed in a reaction with a compound B'Q, in which Q is —NCO, in this structure B'-Z' being B'—NHCOO—. If Y means —COOH in the compound with structure (IIa), a compound with structure (I) is formed in the reaction with B'NCO where B'-Z'— is B'—NH—C (O)—. If Y means —COOH in the compound with structure (IIa), a silane with structure (I) is obtained in a reaction with a compound B'OH, the structural element B'-Z'— of said silane being B'—O—C(O)—. If Y means OH in the compound with structure (IIa), a silane is formed in a reaction with a compound B"COOH or a corresponding activated acid derivative, the structural element B'-Z' of said silane meaning B'—C(O)O—.

Starting from the teaching of the DE 103 49 766.8, a process is provided according to the present invention, for producing oligomeric silanes with an exactly predetermined number of inorganically condensable silyl radicals and of organically polymerizable groups, which silanes are suitable as additive to both organically polymerizable and inorganically condensable silanes as described hereinabove and/or to precondensates/prepolymerisates of such silanes in order to control the degree of cross-linking of the resins or polymers ("ORMOCER®s") that can be obtained therefrom. By adding said silanes to hydrolytically condensable, in given cases also organically polymerizable silanes, e.g. the rheologic characteristics (viscosity, flow behaviour) in the resulting (inorganically condensed, not yet or not yet completely organically polymerized) resin (solvent-free) or lacquer (solvent-containing) can be varied or set, which is usually very important for an application. Furthermore, the later product characteristics, such as strength or modulus of elasticity of the polymers obtained by condensation and organic cross-linking can be influenced, varied and set in an appropriate manner.

In the process according to the present invention, silanes of the structure (IIa) as defined above or partially or completely condensed condensates thereof and/or polymers thereof which have been polymerized via part or all of the contained organic radicals B, are reacted with a compound (IV)

where Q and each Q' independently of each other mean —NCO, —OH, or —C(O)X', where —C(O)X' means a carboxylic acid group or an activated carbonyl compound, particularly is an acid chloride or an acid anhydride, and where Q and/or Q' can be —NCO or —C(O)X', when the silanes of the structure (IIa) or their condensates/polymerisates as defined above comprise groups Y having the meaning —OH, and where Q and/or Q' can be —NCO or —OH—, when the silanes of the structure (IIa) or their condensates/polymerisates as defined above comprise groups Y having the meaning —COOH. Q can also be a portion of a cyclic intramolecular anhydride or an intermolecular mixed anhydride (—C(O)O—C(O)-alkyl, -aryl, or -alkylaryl/arylalkyl)). In exceptional cases (namely only, when Q and Q' each are activated carboxylic acid groups and c is equal to 1, i.e. only in the case that the compound with the structure (IV) is oxalic acid or an activated oxalic acid derivative), $R^5$ can be a single bond and in the remaining cases, it is a "spacer", i.e. an optional radical with c+1 valences. Preferably, $R^5$ comprises or is a chain of carbon atoms, particularly an alkylene chain of 1 to 60 carbon atoms, more preferably 1 to 15 carbon atoms, which carbon chain can be interrupted in given cases by oxygen atoms, sulfur atoms, carbonyl groups, carboxyl groups, amino groups, or amide groups. Instead, $R^5$ can contain one or more rings (cycloalkyl ring, aromatic ring, with or without heteroatoms), comprising in given cases (one) further such carbon chain(s) or have a pure ring structure, e.g. be a phenylene group, a naphthylene group or a diphenylene group. Said rings or said carbon chains can further be substituted in given cases, provided that their substituents do not interfere with the reaction between Q and Y. A cyano or tricyano structure is an example for this. c is preferably 1, but can also be 2, 3, 4, 5, or 6. For example, di-, tri- or tetra-anhydrides, -carboxylic acids (in given cases activated or activatable), isocyanates or -alcohols are commercially available on a large scale. Natural oligomers can likewise be used for the present invention, e.g. sugar molecules. In exceptional cases, c can even mean a higher number than 6.

When Q and/or Q' are portion of a cyclic anhydride, $R^5$ is bonded to Q or Q' via a carbon atom which carries the radical of the cyclic anhydride.

Preferably, Q and Q' are identical.

The compound with the structure (IV) can be mirror-symmetrical, but does not have to be so.

According to a first embodiment of the invention, the process according to the invention provides new silanes having the structure (V)

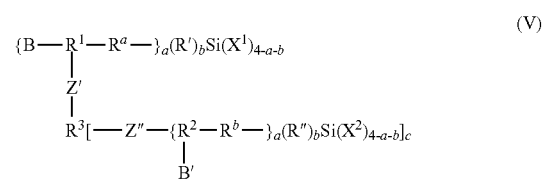

where the radicals and indices have the following meaning:

All radicals $R^a$ and $R^b$ can be identical or different and are independently of each other in each case an open-chain and/or cyclic alkylene, arylene, or alkylene-arylene group, in each case with 1 to 10 carbon atoms, which can be interrupted in some cases by one or more oxygen or sulfur atoms or carboxyl or amino groups or can carry such atoms/groups at their ends opposite the silicon atom.

All radicals $R^1$ and $R^2$ can be equal or different and are independently of each other in each case an open-chain and/or cyclic alkylene, arylene, or alkylene-arylene group, in each case with 1 to 10 carbon atoms, which in some cases can be interrupted by one or more oxygen or sulfur atoms or carboxyl or amino groups or can carry such atoms/groups at one of their ends and which, as can be seen from structure (V), carry the group Z' or Z" as a further substituent.

All radicals $X^1$ and $X^2$ can be identical or different and are independently of each other in each case groups which can enter into a hydrolytic condensation reaction with the formation of Si—O—Si bridges. Thus $X^1$ and $X^2$ are hydrolyzable radicals. They are designated as formers of the inorganic network, because a silicic acid polycondensate network can form in the hydrolytic condensation reaction. With these groups, in interaction with formers of the organic network, present in optional cases, and in this case particularly the organically polymerizable groups of the radicals B and optionally B', physical characteristics of the arising network are set, such as hardness or flexibility or the thermal expansion coefficient. In the literature concerning the inorganic-organic materials containing silicon atoms, e.g. those which are commercially available under the name "ORMOCER®s", much has been written about the respective properties which the respective silane radicals confer to the condensate or to the organically polymerized network so that here no detailed explanations are needed. Preferably, X is a $C_1$-$C_{10}$-alkoxy group, more preferably a $C_1$-$C_4$-alkoxy group and particularly preferably methoxy or ethoxy. However, depending on the requirements, X can also be a halide such as Cl, hydrogen, hydroxy, acyloxy with preferably 2 to 5 carbon atoms, alkylcarbonyl with preferably 2 to 6 carbon atoms, alkoxycarbonyl with preferably 2 to 6 carbon atoms, in given cases also NR" with R" equal to hydrogen, alkyl with preferably 1 to 4 carbon atoms or aryl with preferably 6 to 12 carbon atoms, or any other suitable leaving group.

All radicals R' and R" can be identical or different and are independently of each other in each case an open-chain and/or cyclic alkyl, alkenyl, aryl, or alkylaryl, or arylalkyl group, with preferably 1 to 10 carbon atoms, which in exceptional cases can carry organically polymerizable radicals. As far as the radicals R' and R" are not organically polymerizable, they are designated as network modifiers; depending on their choice, a number of characteristics can also be influenced.

All radicals B and B' can be identical or different; both radicals can have the meaning of a straight-chain or branched organic group with at least one C=C double bond and at least 2, preferably up to 50, carbon atoms. The radicals B and B' carry organically polymerizable groups, optionally selected. The at least one C=C double bond in B or B' can for example be part of a vinyl, allyl, norbornene, acryl and/or methacryl group. In a preferred embodiment, each of the radicals B and B' carries a Michael system, particularly preferably an acrylate or methacrylate group. In a further preferred embodiment, the radical B carries two or even three Michael systems, e.g. acrylate or methacrylate groups. Radicals B and B' which contain $C_2$-$C_4$ alkanediols, the trimethylolpropane group, the pentaerythrite group or the glycerol structure as structural elements are especially to be mentioned. B and B' can be acrylic acid ester groups and/or methacrylic acid ester groups of trimethylolpropane, of glycerol, of pentaerythrite, of the $C_2$-$C_4$-alkanediols, of the polyethylene glycols, of the polypropyleneglycols or of the optionally substituted and/or alkoxylized bisphenol A or can comprise said esters. It to is also preferred that B and in given cases B' contain only one (meth)acrylate group, which is bonded to the remaining molecule via an ester bond of the carboxyl radical. B and B' can comprise an end-to-end carbon skeleton, but the carbon chain(s) (main and/or side chain(s)) can instead be interrupted by heteroatoms or groups such as O, S, SO, NH, NHCO, PR, POR, CONHCO, COO, NHCOO or the like. The carbon skeleton is of B or B' can be exclusively aliphatic, in fact with open and/or closed structures, but B and B' can instead comprise one or more aromatic ring structure(s) or condensed systems or triazine groups or the like, e.g. bisphenol A structures or the like. Furthermore, the groups or structures can be substituted arbitrarily, e.g. with acid, acid amide, ester or amino groups.

All groups Z and Z' independently of each other have the meaning —NH—C(O)O—, —NH—C(O)—, or —CO(O)—, where the two first-mentioned radicals are bonded via the NH group to the radical $R^3$ while the carboxylate group can point in both directions.

In principle, $R^3$ can have the same meaning as $R^5$ in the above-mentioned structure (IV). This means that, if c is larger than 1, said group comprises a corresponding number of bonds to the radicals

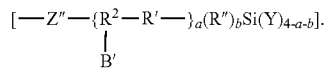

However, it is to be mentioned that in a reaction of a compound having the structure (IV), where Q and/or Q' are part of a cyclic anhydride, a compound with the structure (V) arises in which $R^3$ then of course must carry a carboxylic acid group at its group adjacent to the group Z' or Z".

a means 1 or 2, preferably 1, and b can be 0 or 1.

c is preferably 1, but can also be 2, 3, or 4. In exceptional cases, c can also be 5 or 6 or a larger integer.

The designations "(meth)acrylate, "(meth)acrylic acid radical" and the like are understood in the present context such that alternatively a methacrylate or an acrylate and alternatively a methacrylic acid radical or an acrylic acid radical is present, or the like.

All open chain carbon groups or radicals mentioned in the present patent application can be straight-chained or branched.

In preferred embodiments of the invention, the meanings of R' and R" are identical.

Instead or additionally, the meanings of $R^a$ und $R^b$ and (in given cases also/or) the meaning of $R^1$ and $R^2$ can be identical. Independently thereof, also the meanings of B and B' can be identical; they are, however, not identical in a number of embodiments of the invention.

According to a preferred embodiment, such silanes with structure (V) are produced with the process according to the present invention where B and/or B' have the meaning B"-Z— and Z is a —O—C(O)—, —S—C(O) or —NH—C(O)-group, if Z' and/or Z" are —NH—CO—, and Z is —O—$R^4$, —S—$R^4$, —NH—$R^4$, —C(O)O—$R^4$, —O—, —S—, —NH— oder —C(O)O—, if Z' and/or Z" is —NH—C(O)O—. $R^4$ in these cases can mean alkylene, arylene or alkylarylene with preferably 1 to 10 carbon atoms (for ring-free groups) and 6 to 14 carbon atoms (for ring-containing groups). In these cases, B" such as B and B' is a straight-chain or branched organic group with at least one C=C double bond and 2 to preferably 50 carbon atoms. B" preferably has the meanings which are also mentioned as preferred for B and B'.

The silanes with structure (V) according to the present invention as well as silicic acid polycondensates thereof which have not yet completely been condensed can be hydrolyzed or condensed, either partly or further or completely, alone or in given cases also with further silanes and/or silicic acid (partial) polycondensates. Suitable as further silanes or further silicic acid (partial) polycondensates are, on the one hand, silanes and (partial) precondensates thereof which are co-condensable, but not co-polymerizable, or, on the other hand, such silanes and (partial) precondensates thereof which also have polymerizable groups available. By cross-linking with the silanes according to the invention, 2, 3 or even more inorganically condensable or organically polymerizable or, rather, inorganically condensed and organically polymerizable molecular structures, are bonded to each other, which finally results in a considerable increase of the cross-linking density as well as of the molecular weight and consequently has a drastic influence on the material properties. Thus, e.g. already by a small portion of functionalized siloxane having structure (V) (see also example 1) which is cross-linked and functionalized by means of 1,6-diisocynatooctane, a considerable increase in strength after both dry storage and wet storage subsequent to the organic polymerization is observed, compared to the corresponding non-cross-linked material. The cross-linking entity is of organic nature and variable in length, structure and composition, for which reason the property profiles can be selectively modified therewith (in addition to the two inorganically and organically polymerizable molecular portions). Thus, e.g. aromatic structures can be used for increasing the refractive index and for stiffening, and further functional groups can be introduced.

Besides, the compounds with the structure (V) are valuable as additives (modifiers) in at least partially inorganically condensed, however not yet or only partially polymerized resin systems made from the above-specified silane components and in given cases further components, where they can be used for controlling the rheologic characteristics like viscosity or flow behaviour, as has already been described in detail hereinabove.

Furthermore, by using the process according to the invention, the hardening of inorganically condensable and in given cases organically polymerizable silanes having structure (IIa) as defined hereinabove and thus comprising a free (or in given cases protected/re-esterified) hydroxy or carboxyl group can be graduated in a very dosed manner by adding a quantity of compound (IV) which is stoichiometric or to a desired extent below stoichiometry in relation to the Y groups of the compounds or (partial) condensates with structure (IIa). By means of the cross-linking or a cross-linking portion thus effected to a desired extent, not only the later product characteristics of the polymer which has organically polymerized via the groups B, B', such as strength or modulus of elasticity, can be varied and set in a desired range, but also desired rheologic characteristics, such as flow behaviour or viscosity of the initially (and only) inorganically (partially) condensed resin or lacquer can be set, which thus can be tailored for many applications. It is very important to have this possibility available. Moreover, a hardening amplified by an additional step is possible, which can be very useful in certain cases: Thus, for example, a precondensation of the inorganically condensable silanes of the structure (IIa) to a precondensed resin can take place in the $1^{st}$ stage, the cross-linking of said resin being intensified subsequently (e.g. after application in the form of a layer) in a $2^{nd}$ stage by using the process according to the invention at room temperature or at a higher temperature (e.g. to provide a non-adhesive layer). In a possible $3^{rd}$ stage, a polymerization of the organically polymerizable groups takes place (e.g. a radically initiated polymerization of double-bond-containing groups; thiol-en-polyaddition) (final hardening). At least in case of the reaction of condensates obtained from OH-containing silanes, the $2^{nd}$ stage as a rule is performed by a two-component processing, as for the case of reacting an OH group with an OCN group, a reaction usually takes place already at room temperature at the time of bringing them together although in given cases relatively slowly. If this is to be avoided, a capped —OCN compound can be added, the —OCN group being released at a higher temperature. Then, the precondensated silane resin can be stored at room temperature together with the compound $Q-R^5[-Q']_c$, and the second stage of the reaction is initiated when needed, e.g. after application of the resin as a layer onto a surface or a substrate, by using heat. By the way, in given cases the stages 2 and 3 can also be interchanged.

Additionally, copolymerizable, preferably purely organical components can be added to the silanes according to structure (V) as well as to silicic acid polycondensates or partial polycondensates thereof which are not completely condensed yet, where said copolymerizable components, for example, can be radically and/or ionically and/or covalent-nucleophilically polymerizable compounds. Radically polymerizable compounds which can be added are, for example, those with C=C double bonds such as, for example, acrylates or methacrylates where the polymerization is done via the C=C double bonds. Ionically polymerizable compounds which can be added comprise, for example, ring systems which are polymerizable by cationic ring opening such as, for example, spiroorthoesters, spiroorthocarbonates, bicyclic spiroorthoesters, monoepoxides or oligoepoxides or spirosilanes or condensates thereof such as, for example, known from DE 41 25 201 C1. Instead, compounds can be added which are ionically as well as radically polymerizable such as, for example, methacryloyl-spiroorthoesters. These are polymerizable radically via the C=C double bond and cationically under ring opening. The production of these systems is described, for example, in the Journal f. prakt. Chemie, Volume 330, Issue 2, 1988, pages 316-318. Furthermore, it is, for example, possible to add other known silane-bonded cyclic systems which can be copolymerized thereto. Such systems are, for example, those which comprise epoxides. Such systems are described in the production of the spirosilanes in DE 41 25 201 C1. The aforementioned components are copolymerized via their organically polymerizable groups during the polymerization of the resins so that a copolymerizate consisting of silanes according to the invention and copolymers can be obtained the silane groups of which have been hydrolytically condensed or partially condensed with one another or with additional groups. Further possibilities of modification result from the use of the inventive silanes with the structure (V) in such materials as they are described for example in the European patent specifications EP 668 326 B1, EP 618 242 B1 and in the German patent specification DE 41 33 494 C2.

Particularly as a result of the processing which can be handled particularly sensibly due to the possibility to separate the three production stages from each other and to carry them out as and when needed, the (pre-)condensates/(pre-)polymerisates made from or with silanes of the structure (IIa) which were obtained from or using the silanes of the structure (V) or, rather, by using the compounds $Q-R^5[-Q']_c$, are suitable e.g. as or for the production of coating, filling, adhesive, casting and sealing materials, fibers, particles, films, binding agents for ceramic particles, or embedded materials, from which very scratch-resistant coatings and shaped bodies having high strength can be manufactured. Particularly, unfilled polymer materials (polymerisates) as well as (filled) composites can be obtained, which were obtained from resins having relatively low viscosity, and which have very low shrinkage. Reference is also made to such embodiments in which the resins and polymerisates or composites, respectively, are monomer-free and therefore toxicologically/allergically harmless, particularly when they additionally have high wet strength (see above).

In a special embodiment of the invention, the silicic acid polycondensate or partial condensate is mixed with one or more additives and/or fillers, in fact preferably prior to the $2^{nd}$ stage of hardening as mentioned hereinbefore, but in given cases instead between the $2^{nd}$ and the $3^{rd}$ stage.

The materials for such fillers are not critical and are selected depending on the requirements. Materials such as used in the fillers according to the documents DE 196 43 781, DE 100 41 038 or DE 100 18 405 suit well. $SiO_2$ particles which can be obtained for example according to known sol-gel processes and which can then have a very narrow diameter distribution, suit very well. These particles or differently composed particles can be modified on their surface, e.g. silanized, in order to adapt their surface characteristics to those of the matrix.

Among others, macrofillers (e.g. from glass, ceramics or quartz, with particle sizes between 2 to 50 μm), homogeneous microfillers (e.g. from pyrogenic silicic acid, with particle sizes about 0.04 μm), inhomogeneous microfillers (example: a part of the pyrogenic silicic acid is present as fragmented polymerisate, hybrid fillers (mixtures of macro- and microfillers) or finest hybrid fillers (e.g. mixtures of aerosil and Ba or Sr glass with a particle size in the range of about 1 to 5 μm) can be used as further filling materials. For example, glass particles with particle diameters of around 1-5 μm, or glass fibers suit very well for the present invention.

Alternatively or additionally, nanoparticular fillers of different size or different composition can be used. "Nanoparticular" in this context means that the fillers have a diameter or their largest diameter in the range of below 1000 nm, for fillers with a broader particle size distribution, at least 90% of the filler material shall be below said limit. Preferably nanoparticular fillers having nearly spherical shape are used. More preferably fillers having a diameter in the range of 10 to 400 nm and even more preferably in the range of 10 to 100 nm are used. Further, it is preferred to use fillers having a narrow particle size.

The relation of the fillers with respect to each other can be selected arbitrarily. Weight portions of the nanoparticular filler of around 5 to around 60% by weight in relation to the total weight of the filler in the composite are favourable.

Portions of more than 5 to 30% by weight are particularly favourable. It has turned out that particularly highly filled composites which have a particularly low shrinkage and a particularly high abrasion resistance, can be obtained when using portions in said range.

Depending on the field of application, an arbitrarily selected quantity of the filler up to about 90% of the total weight can be used.

Examples for further additives are coloring agents (dyes or pigments), oxidation inhibitors, flow-control agents, UV absorbers, stabilizers or additives to increase the conductivity (e.g. graphite powder, silver powder).

The invention will be explained in more detail below with the aid of preparation examples.

EXAMPLE 1

This example shows the production of a compound of the structure (IIa) or the re-esterification product thereof with b equal to 1.

Reaction of 3-glycidyloxypropylmethyldiethoxysilane with methacrylic acid (MAS):

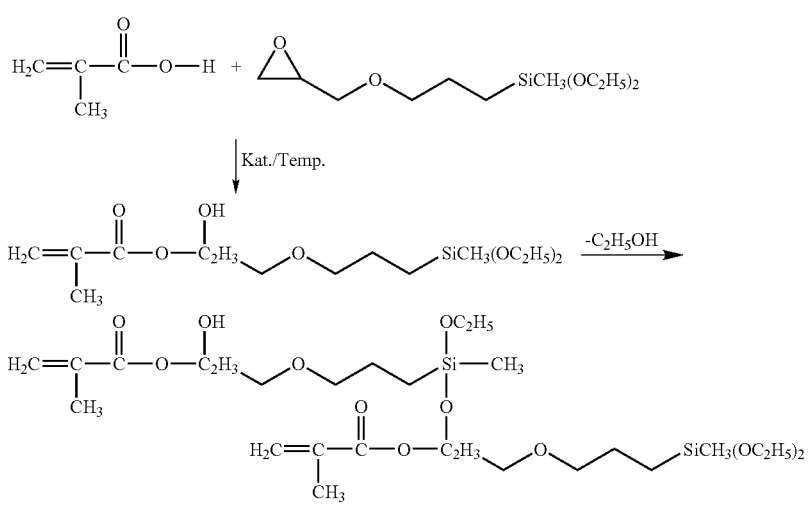

Triphenylphosphane as an addition catalyst, BHT as a stabilizer, and subsequently 47.35 g (0.550 mol) of methacrylic acid are added dropwise under a dry atmosphere (oxygen) to a receiving flask containing 125.0 g (0.503 mol) of 3-glycidyloxypropylmethyl-dimethoxysilane, and stirred at 80° C. (for ca. 24 hours). The reaction can be tracked via the reduction of the carboxylic acid concentration by means of acid titration as well as the epoxide conversion by means of Raman spectroscopy/epoxide titration. The band characteristics for the epoxide group of the epoxy silane appear in the Raman spectrum at 1256 cm$^{-1}$. The epoxide and carboxylic acid conversion is ≧99% or ≧89%, respectively, (a consequence of the carboxylic acid excess).

EXAMPLE 2

This example shows the hydrolysis and condensation reaction of the product from example 1.

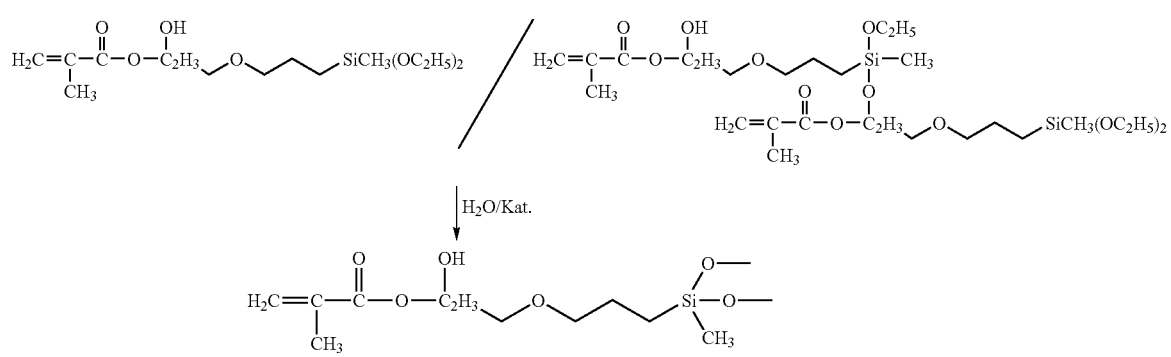

After the addition of ethyl acetate (1000 ml/mol of silane) and $H_2O$ for the hydrolysis including HCl as catalyst, the mixture is stirred at 30° C. The course of the hydrolysis is tracked by water titration. After stirring for several days, the workup is done by repeated shaking with aqueous NaOH, and subsequently shaking with water, and filtering over a hydrophobized filter. After this, solvents are evaporated in a rotary evaporator. Then the remaining solvents (alcohol, water) are drawn off in an oil pump vacuum. A resin results which is liquid without the use of reactive diluents (monomers) and which has a very low viscosity of ca. 4-6 Pa·s at 25° C. (largely depending on the exact hydrolysis and workup conditions) and 0.00 mmol of $CO_2H/g$ (no free carboxyl groups present any more).

EXAMPLE 3a

This example shows the addition of a symmetrical diisocyanate to the hydroxy group of the product of example 2, yielding a resin system.

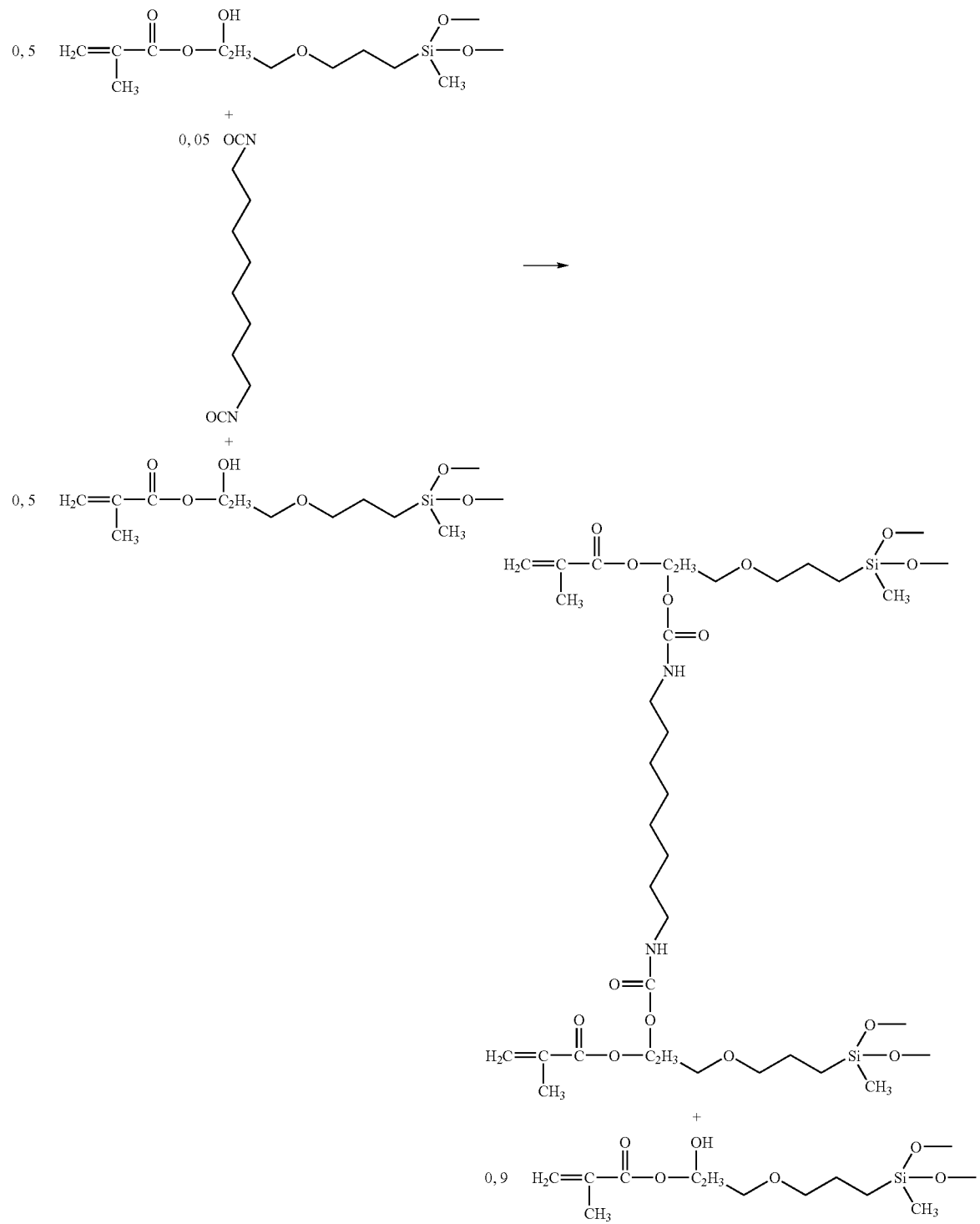

0.39 g (0.002 mol) of 1,8-diisocyanatooctane are added dropwise under a dry atmosphere (oxygen) at room temperature with stirring to a receiving flask containing 10.57 g (0.04 mol) of the above resin, and stirred at 30° C. The reaction can be tracked via the reduction of the OCN band by means of the IR spectrum. The band characteristic of the OCN group appears in the IR spectrum at 2273 cm$^{-1}$. A viscous resin with a viscosity of ca. 14 Pa·s at 25° C. is obtained (largely depending on the exact synthesis and workup conditions, particularly also of the precursors).

IR-Data:
- $v_{(OH \leftarrow educt)} \approx 3400$ cm$^{-1}$ (unreacted OH since reaction was only with 0.05 moles of methacrylic acid isocyanatoethylester)
- $v_{(NH \leftarrow urethane)} \approx 3340$ cm$^{-1}$ (shoulder on the OH signal)
- $v_{(C=O \leftarrow methacrylate/urethane)} \approx 1720$ cm$^{-1}$
- $v_{(C=C \leftarrow methacrylate)} \approx 1638$ cm$^{-1}$

EXAMPLE 3b

Example 3a was repeated with the modification that instead of 0.002 mol diisocyanatooctane, 0.004 mol diisocyanatooctane were used. A viscous resin with a viscosity of ca. 48 Pa·s at 25° C. is obtained (largely depending on the exact synthesis and workup conditions, particularly also of the precursors).

IR data:
- $v_{(OH \leftarrow educt)} \approx 3400$ cm$^{-1}$ (unreacted OH since reaction was only with 0.10 moles of methacrylic acid isocyanatoethylester)
- $v_{(NH \leftarrow urethane)} \approx 3340$ cm$^{-1}$ (shoulder on the OH signal)
- $v_{(C=O \leftarrow methacrylate/urethane)} \approx 1720$ cm$^{-1}$
- $v_{(C=C \leftarrow methacrylate)} \approx 638$ cm$^{-1}$ A comparison of the resin systems of the examples 3a and 3b shows exemplarily that the viscosity (14 or 48 Pa·s) can be set by the proportion of the cross-linking reagent (in this case 1,8-diisocyanatooctane) with regard to the application. A respective setting is also possible via the chain length of the cross-linking reagent, its structure and the number of cross-linking groups.

EXAMPLES 3c TO 3e 0.016 mol 1,8-diisocyanatooctane (→resin system 3c); as an addition catalyst 1.25% DBTL as well as 0.014 mol 1,8-diisocyanatooctane (→resin system 3d); 0.010 mol 1,8-diisocyanatooctane (→resin system 3e) are added under dry atmosphere (oxygen) at room temperature to a receiving flask containing 10.6 g (0.04 mol) of the above resin. The reaction can be tracked via the reduction of the OCN band by means of the IR spectrum. The band characteristic of the OCN group appears in the IR spectrum at 2273 cm$^{-1}$ and disappears after the reaction is complete.

For the synthesis of the resin system 3c, the actual reaction takes place at 50° C., and it is isolated in the form of a non-tacky reaction product (after ca. 1 to 2 days).

For the synthesis of the resin system 3d, the actual reaction takes place at room temperature, and it is isolated in the form of a non-tacky reaction product (after ca. 30 min).

For the synthesis of the resin system 3e, the actual reaction takes place at 50° C., and it is isolated in the form of a still tacky reaction product (after ca. 1 day).

As the example of the resin systems 3c to 3e shows, a consistency of still tacky up to tack-free can be set by variation of the cross-linking reagent 1,8-diisocyanatooctane in the range of high proportions. The cross-linking time with regard to the application of the above mixtures (e.g. as layer or shaped body) prior to the subsequent final hardening can be set in the range of minutes to days (by radical polymerization, compare with example 4).

EXAMPLE 4

This example describes the polymerization of the organically polymerizable groups of the product from example 3a.

The resin system 3a containing 1% Lucirin TPO is shaped as a rod (2×2×25 mm$^3$). The methacrylate groups are reacted in the course of a photoinduced radical polymerization, in which the resin hardens. By means of a 3-point bending experiment, the modulus of elasticity as well as the fracture strength of the resulting rods is determined after 1.5 days under air or water at 40° C.

| Modulus of elasticity | ca. 1.88 GPa (air)/1.34 GPa (water) |
| Fracture strength | ca. 90 MPa (air)/64 MPa (water) |

Using a cross-linking agent (1,8-diisocyanatooctane) of only 0.05 mole portions, markedly increased strength values as compared to the basic matrix (see example 2 and comparative example 1) are obtained with a still very low viscosity of the resin. Since, in addition to this, the matrix system is free of monomers and has a viscosity favourable with regard to processing, a use for dental composites is particularly suitable.

COMPARATIVE EXAMPLE 1

Resin from example 1b containing 1% Lucirin TPO is shaped as a rod (2×2×25 mm$^3$). The methacrylate groups are reacted in the course of a photoinduced radical polymerization, in which the resin hardens. By means of a 3-point bending experiment, the modulus of elasticity as well as the fracture strength of the resulting rods is determined after 1.5 days under air or water at 40° C.

| Modulus of elasticity | ca. 1.74-1.89 GPa (air)/1.12-1.13 GPa (water) |
| Fracture strength | ca. 70-80 MPa (air)/45-50 MPa (water) |

The invention claimed is:

1. A process for reacting a silane with the structure (IIa)

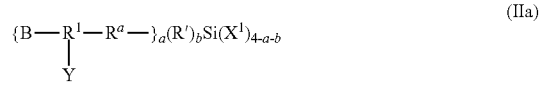

(IIa)

or a re-esterification product, or, in the case X$^1$ is an alkoxy group, a condensation product of said silane formed by the loss of an alcohol molecule, where the radicals and indices have the following meanings R$^a$ is an open-chain and/or cyclic alkylene, arylene, or alkylene-arylene group having 1 to 10 carbon atoms in each case, which can be interrupted by one or more oxygen or sulfur atoms or carboxyl or amino groups or can carry such atoms/groups at its end opposite the silicon atom, R$^1$ is an open-chain and/or cyclic alkylene, arylene, or alkylene-arylene group having 1 to 10 carbon atoms in each case, substituted with Y, which can be interrupted by one or more oxygen or sulfur atoms or carboxyl or amino groups or can carry such atoms/groups at one of its ends, R' is an open-chain and/or cyclic alkylene, arylene, or alkylene-arylene group, B has the meaning of a straight-chain or branched organically polymerizable group with at least one C=C double bond and at least 2 carbon atoms, $X^1$ is a group which can enter into a hydrolytic condensation reaction under formation of Si—O—Si bridges, Y means —OH or —COOH, a is 1 or 2, and b is 0 or 1, via reaction at group Y with a compound having the structure (IV)

where each of Q and each Q' independently means —NCO, —OH, or —C(O)X', where —C(O)X' means a carboxylic acid, an acid anhydride or an activated carbonyl compound in which X' is a chloride and where each of Q and Q' independently can be —NCO or —C(O)X', when the silanes of structure (IIa) as defined above comprise groups Y having the meaning —OH, and where each Q and Q' independently can be —NCO or —OH—, when the silanes of structure (IIa) as defined above comprise groups Y having the meaning —COOH, where $R^5$ means a single bond only when each of Q and Q' independently are activated carboxylic acid groups and c is equal to 1, otherwise $R^5$ is a radical with c+1 valences, where c is 1 or an integer greater than 1;

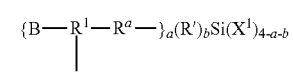

wherein said component (III) repeats twice, in triplicate or in a higher quantity, where the radicals B, $R^1$, $R^a$, R', $X^1$ and the indices a and b are defined as above for structure (IIa) and can be identical or different for each occurrence of component (III).

2. The process according to claim 1, wherein each of Q and Q' independently in structure (IV) is selected from among acid chlorides and acid anhydrides.

3. The process according to claim 1, wherein each of Q and Q' independently in structure (IV) is an isocyanate group.

4. A silane of the following structure (V)

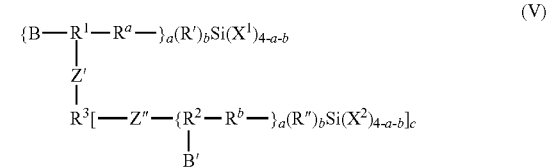

where:

B has the meaning of a straight-chain or branched organically polymerizable group with at least one C=C double bond and at least 2 carbon atoms, $R^1$ is an open-chain and/or cyclic alkylene, arylene, or alkylene-arylene group having 1 to 10 carbon atoms in each case, that is bound to Z' and that can be interrupted by one or more oxygen or sulfur atoms or carboxyl or amino groups or can carry such atoms/groups at one of its ends, $R^a$ is an open-chain and/or cyclic alkylene, arylene, or alkylene-arylene group having 1 to 10 carbon atoms in each case, which can be interrupted by one or more oxygen or sulfur atoms or carboxyl or amino groups or can carry such atoms/groups at its end opposite the silicon atom, R' is an open-chain and/or cyclic alkyl, alkenyl, aryl, or alkylaryl, or arylalkyl group, $X^1$ is a group which can enter into a hydrolytic condensation reaction under formation of Si—O—Si bridges, $R^2$ is an open-chain and/or cyclic alkylene, arylene, or alkylene-arylene group having 1 to 10 carbon atoms in each case, that is bound to Z" and that can be interrupted by one or more oxygen or sulfur atoms or carboxyl or amino groups or can carry such atoms/groups at one of its ends, $R^b$ is an open-chain and/or cyclic alkylene, arylene, or alkylene-arylene group having 1 to 10 carbon atoms in each case, which can be interrupted by one or more oxygen or sulfur atoms or carboxyl or amino groups or can carry such atoms/groups at its end opposite the silicon atom, R" is an open-chain and/or cyclic alkyl, alkenyl, aryl, or alkylaryl, or arylalkyl group, $X^2$ is a group which can enter into a hydrolytic condensation reaction under formation of Si—O—Si bridges, B' has the meaning of a straight-chain or branched organically polymerizable group with at least one C=C double bond and at least 2 carbon atoms, Z' and Z" are independently selected from the group consisting of —NH—C(O)O— bonded to the radical $R^3$ via the NH-group, —NH—C(O)— bonded to the radical $R^3$ via NH-group, or —CO(O)— bonded to the radical $R^3$ via either the C— or O— atom, $R^3$ means a single bond when c is equal to 1 and Z' and Z" are —C(O)O, bonded to the radicals $R^1$ and $R^2$ respectively through an oxygen atom otherwise, $R^3$ is an arbitrarily selected radical which has c+1 valences, a is 1 or 2, b is 0 or 1, and c is 1 or an integer greater than 1.

5. The silane according to claim 4, where $R^3$ represents a hydrocarbon radical, particularly an open-chain and/or cyclic alkylene, arylene, or alkylene-arylene group having 1 to 30 carbon atoms in each case, more preferably having 1 to 15 carbon atoms, which can optionally be interrupted by one or more oxygen or sulfur atoms or carbonyl, carboxyl, amino or amide groups, and which in the case that c is larger than 1, has a corresponding number of bonds to the radicals

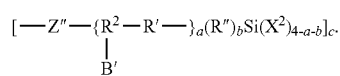

6. The silane according to claim 4, in which each of R' and R" independently represents a group having 1 to 10, preferably 1 to 4, carbon atoms and each of B and optionally B' carry at least one Michael system, selected from an acrylate or methacrylate group, and each of $X^1$ and $X^2$ independently is a $C_1$-$C_{10}$-alkoxy group.

7. The silane according to claim 5, in which
each of the radicals B and optionally B' independently are acrylic acid ester groups or methacrylic acid ester groups of trimethylolpropane, glycerin, pentaerythritol, $C_2$-$C_4$-alkane diol, polyethylene glycol, polypropylene glycol, or an optionally substituted and/or alkoxylated bisphenol A.

8. The silane according to claim 4, in which each of the radicals B and optionally B' independently comprise an end-to-end carbon skeleton or said skeleton is interrupted by heteroatoms or groups chosen from among O, S, SO, NH, NHCO, PR, POR, CONHCO, COO, NHCOO.

9. The silane according to claim 4, in which a is equal to 1 and b is equal to 0.

10. The silane according to claim 4, in which a is equal to 1 and b is equal to 1.

11. The silane according to claim 4, in which each of B and B' independently is a (meth)acrylate group or comprises a radical which is bonded via a (meth)acrylate group to $R^1$ or $R^2$ and comprises no additional (meth)acrylate ester groups.

12. A condensate or a partial condensate, comprising the following structural unit (VI)

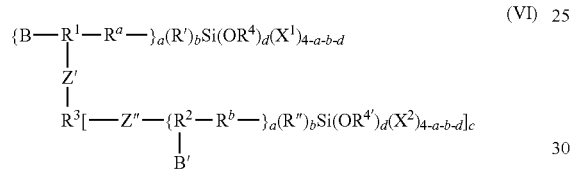

(VI)

where:
B has the meaning of a straight-chain or branched organically polymerizable group with at least one C═C double bond and at least 2 carbon atoms,
B' has the meaning of a straight-chain or branched organically polymerizable group with at least one C═C double bond and at least 2 carbon atoms,
$R^1$ is an open-chain and/or cyclic alkylene, arylene, or alkylene-arylene group having 1 to 10 carbon atoms in each case, that is bound to Z' and that can be interrupted by one or more oxygen or sulfur atoms or carboxyl or amino groups or can carry such atoms/groups at one of its ends,
$R^2$ is an open-chain and/or cyclic alkylene, arylene, or alkylene-arylene group having 1 to 10 carbon atoms in each case, that is bound to B' and that can be interrupted by one or more oxygen or sulfur atoms or carboxyl or amino groups or can carry such atoms/groups at one of its ends,
$R^3$ means a single bond when c is equal to 1 and Z' and Z" are —C(O)O, bonded to the radicals $R^1$ and $R^2$ respectively through an oxygen atom otherwise, $R^3$ is an arbitrarily selected radical which has c+1 valences,
$R^4$ has the meaning of a bond to another silicon atom, optionally instead of this partially also to another metal atom which can be inserted to silicic acid heteropolycondensates, and in given cases can partly instead be hydrogen,
$R^{4'}$ has the meaning of a bond to another silicon atom, optionally instead of this partially also to another metal atom which can be inserted to silicic acid heteropolycondensates, and in given cases can partly instead be hydrogen,
$R^a$ is an open-chain and/or cyclic alkylene, arylene, or alkylene-arylene group having 1 to 10 carbon atoms in each case, which can be interrupted by one or more oxygen or sulfur atoms or carboxyl or amino groups or can carry such atoms/groups at its end opposite the silicon atom,
$R^b$ is an open-chain and/or cyclic alkylene, arylene, or alkylene-arylene group having 1 to 10 carbon atoms in each case, which can be interrupted by one or more oxygen or sulfur atoms or carboxyl or amino groups or can carry such atoms/groups at its end opposite the silicon atom,
R' is an open-chain and/or cyclic alkyl, alkenyl, aryl, or alkylaryl, or arylalkyl group,
R" is an open-chain and/or cyclic alkyl, alkenyl, aryl, or alkylaryl, or arylalkyl group,
$X^1$ is a group which can enter into a hydrolytic condensation reaction under formation of
Si—O—Si bridges,
$X^2$ is a group which can enter into a hydrolytic condensation reaction under formation of
Si—O—Si bridges,
Z' and Z" are independently selected from the group consisting of —NH—C(O)O— bonded to the radical $R^3$ via the NH-group, —NH—C(O)— bonded to the radical $R^3$ via NH-group, or —CO(O)— bonded to the radical $R^3$ via either the C— or O— atom,
a is 1 or 2,
b is 0 or 1,
c is 1 or an integer greater than 1, and
d is 1, 2 or 3.

13. The condensate or the partial condensate according to claim 12, where the condensate comprises at least 30 mol-%, preferably at least 50 mol-%, more preferably at least 70 mol-%, even more preferably at least 90 mol-% and particularly preferably 100 mol-% of the structural unit (VI).

14. The condensate or the partial condensate according to claim 12, further comprising a particle-shaped filler.

15. A polymerisate or a partial polymerisate, comprising the following structural unit (VII)

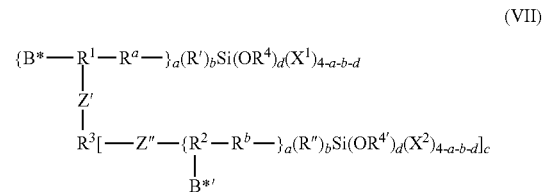

(VII)

where:
B* is a straight-chain or branched organically polymerizable group with at least one C═C double bond and at least 2 carbon atoms, or such a straight-chain or branched organically polymerizable group, the double bond of which has already reacted,
B*' is a straight-chain or branched organically polymerizable group with at least one C═C double bond and at least 2 carbon atoms, or is such a straight-chain or branched organically polymerizable group, the double bond of which has already reacted,
$R^1$ is an open-chain and/or cyclic alkylene, arylene, or alkylene-arylene group having 1 to 10 carbon atoms in each case, that is bound to Z' and that can be interrupted by one or more oxygen or sulfur atoms or carboxyl or amino groups or can carry such atoms/groups at one of its ends, $R^2$ is an open-chain and/or cyclic alkylene, arylene, or alkylene-arylene group having 1 to 10 carbon atoms in each case, that is bound to B*" and that can be interrupted by one or more oxygen or sulfur atoms or carboxyl or amino groups or can carry such atoms/groups at one of its ends, $R^3$ means a single bond when c is equal to 1 and Z' and Z" are —C(O)O bonded to the radicals $R^1$ and $R^2$ respectively through an oxygen atom, otherwise, $R^3$ is an arbitrarily selected radical which has c+1 valences, $R^4$ has the meaning of a bond to another silicon atom, optionally instead of this partially also to another metal atom which can be inserted to silicic acid heteropolycondensates, and in given cases can partly instead be hydrogen, $R^{4'}$ has the meaning of a bond to another silicon atom, optionally instead of this partially also to another metal atom which can be inserted to silicic acid heteropolycondensates, and in given cases can partly instead be hydrogen, $R^a$ is an open-chain and/or cyclic alkylene, arylene, or alkylene-arylene group having 1 to 10 carbon atoms in each case, which can be interrupted by one or more oxygen or sulfur atoms or carboxyl or amino groups or can carry such atoms/groups at its end opposite the silicon atom, $R^b$ is an open-chain and/or cyclic alkylene, arylene, or alkylene-arylene group having 1 to 10 carbon atoms in each case, which can be interrupted by one or more oxygen or sulfur atoms or carboxyl or amino groups or can carry such atoms/groups at its end opposite the silicon atom, R' is an open-chain and/or cyclic alkyl, alkenyl, aryl, or alkylaryl, or arylalkyl group, R" is an open-chain and/or cyclic alkyl, alkenyl, aryl, or alkylaryl, or arylalkyl group, $X^1$ is a group which can enter into a hydrolytic condensation reaction under formation of Si—O—Si bridges, $X^2$ is a group which can enter into a hydrolytic condensation reaction under formation of Si—O—Si bridges, Z' and Z" are independently selected from the group consisting of —NH—C(O)O— bonded to the radical $R^3$ via the NH-group, —NH—C(O)— bonded to the radical $R^3$ via NH-group, or —CO(O)— bonded to the radical $R^3$ via either C— or O—, a is 1 or 2,
b is 0 or 1,
c is 1 or an integer greater than 1, and
d is 1, 2 or 3.

16. The polymerisate or the partial polymerisate according to claim 15, wherein the polymerisate comprises at least 30 mol-%, preferably at least 50 mol-%, more preferably at least 70 mol-%, even more preferably at least 90 mol-% and particularly preferably 100 mol-% of the structural unit (VII).

17. The polymerisate or the partial polymerisate according to claim 15, further comprising a particle-shaped filler.

18. A process for reacting a condensate, a partial condensate, a polymer or a partial polymer comprising structural units having structure (IIb)

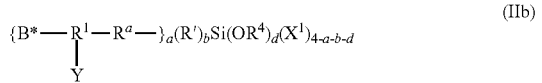
(IIb)

wherein $R^1$, $R^a$, R', $X^1$, and Y can be identical or different and have following meaning:

$R^a$ is an open-chain and/or cyclic alkylene, arylene, or alkylene-arylene group having 1 to 10 carbon atoms in each case, which can be interrupted by one or more oxygen or sulfur atoms or carboxyl or amino groups or can carry such atoms/groups at its end opposite the silicon atom, $R^1$ is an open-chain and/or cyclic alkylene, arylene, or alkylene-arylene group having 1 to 10 carbon atoms in each case, substituted with Y, which can be interrupted by one or more oxygen or sulfur atoms or carboxyl or amino groups or can carry such atoms/groups at one of its ends, R' is an open-chain and/or cyclic alkyl, alkenyl, aryl, or alkylaryl, or arylalkyl group, B* is a straight-chain or branched organically polymerizable group with at least one C=C double bond and at least 2 carbon atoms, or is such a straight-chain or branched organically polymerizable group, the double bond of which has already reacted, $X^1$ is a group which can enter into a hydrolytic condensation reaction under formation of Si—O—Si bridges, Y means —OH or —COOH, and $R^4$ has the meaning of a bond to another silicon atom, optionally instead of this partially also to another metal atom which can be inserted to silicic acid heteropolycondensates, and in given cases can partly instead be hydrogen, a is 1 or 2,
b is 0 or 1, and
d is 1, 2 or 3, wherein said condensate, a partial condensate, a polymer, or a partial polymer comprising structural units of structure (IIb), is reacted via reaction at group Y with a compound having the structure (IV)

$$Q-R^5[-Q']_c,$$ (IV)

where each of Q and Q' independently means —NCO, —OH, or —C(O)X', where —C(O)X' means a carboxylic acid, an acid anhydride or an activated carbonyl compound in which X' is a chloride and where each of Q and Q' can be —NCO or —C(O)X', when the condensates or a polymerisate of structure (IIb) as defined above comprises groups Y having the meaning —OH, and where each of Q and Q' independently can be —NCO or —OH—, when the condensates/polymerisates of structure (IIb) as defined above comprise groups Y having the meaning —COOH, where $R^5$ means a single bond only when each of Q and Q' independently are activated carboxylic acid groups and c is equal to 1, otherwise $R^5$ is a radical with c+1 valences wherein c is 1 or an integer greater than 1.

19. The process according to claim 18, where each of Q and Q' independently in structure (IV) is selected from among acid chlorides and acid anhydrides.

20. The process according to claim 18, where each of Q and Q' independently in structure (IV) is an isocyanate group.

21. The process according to claim 18, where $R^5$ comprises or is a chain of carbon atoms which can be interrupted by oxygen atoms, sulfur atoms, carbonyl groups, carboxyl groups, amino groups, or amide groups, or where $R^5$ contains one or more rings or has a ring structure, wherein the said rings or carbon chains can further be substituted, or where, under the proviso that each of Q and Q' independently is a carboxylic acid or an activated carboxylic acid and c is 1, then $R^5$ can be a single bond.

22. The process according to claim 1, where $R^5$ comprises or is a chain of carbon atoms which can be interrupted by oxygen atoms, sulfur atoms, carbonyl groups, carboxyl groups, amino groups, or amide groups, or where $R^5$ contains one or more rings or has a ring structure, wherein the said ring(s) or carbon chain can further be substituted, or where, under the proviso that each of Q and Q' independently is a carboxylic acid or an activated carboxylic acid and c is 1, then $R^5$ can be a single bond.

* * * * *

UNITED STATES PATENT AND TRADEMARK OFFICE
CERTIFICATE OF CORRECTION

PATENT NO. : 8,076,441 B2
APPLICATION NO. : 11/910862
DATED : December 13, 2011
INVENTOR(S) : Herbert Wolter It is certified that error appears in the above-identified patent and that said Letters Patent is hereby corrected as shown below:

IN THE SPECIFICATION

Column 4, lines 16, 36 and 42, please replace "IfY" with --If Y--.

Column 7, line 18, please replace "alkoxylized bisphenol A or can compromise said esters. It to is" with --alkoxylized bisphenol A or can compromise said esters. It is--.

Column 7, line 26, please replace "carbon skeleton is of B or B' can be exclusively aliphatic, in" with --carbon skeleton of B or B' can be exclusively aliphatic, in--.

IN THE CLAIMS

Column 15, line 33, please replace "$V_{(C=C \leftarrow methacrylate)} \approx 638 \text{ cm}^{-1}$" with --$V_{(C=C \leftarrow methacrylate)} \approx 1638 \text{ cm}^{-1}$--.

Column 18, lines 56-60, please replace "$\begin{array}{c} [-Z''-\{R^2-R'-\}_a(R'')_b Si(X^2)_{4-a-b}]_{c_1} \\ | \\ B' \end{array}$" with --$\begin{array}{c} [-Z''-\{R^2-R^b-\}_a(R'')_b Si(X^2)_{4-a-b}]_{c_1} \\ | \\ B' \end{array}$--.

Signed and Sealed this
Nineteenth Day of February, 2013

Teresa Stanek Rea
*Acting Director of the United States Patent and Trademark Office*